United States Patent [19]

Wiesner

[11] 4,212,830

[45] Jul. 15, 1980

[54] PROCESS FOR PREPARING INSECT PHEROMONES

[76] Inventor: Charles J. Wiesner, 123 McKeen St., Fredericton, New Brunswick, Canada, E3A 2P9

[21] Appl. No.: 961,156

[22] Filed: Nov. 16, 1978

Related U.S. Application Data

[62] Division of Ser. No. 808,420, Jun. 20, 1977.

[30] Foreign Application Priority Data

Jan. 28, 1977 [CA] Canada .................................. 270624

[51] Int. Cl.$^2$ ............................................. C07C 47/20
[52] U.S. Cl. .................................................... 568/486
[58] Field of Search ...................... 260/601 R; 426/65

[56] References Cited

U.S. PATENT DOCUMENTS

3,821,421   6/1974   Bergeman et al. ............... 260/601 R

*Primary Examiner*—Werren B. Lone
*Attorney, Agent, or Firm*—Ladas, Parry, Von Gehr, Goldsmith & Deschamps

[57] ABSTRACT

The specification discloses a novel process for the preparation of 11-tetradecenal and novel intermediates therefor. There is also disclosed processes for the intermediates. The novel intermediates include 1,1-dialkoxy-9-halo-nonane and 1,1-dialkoxy-11-tetradecene. There is further disclosed a process for preparing a mixture of cis- and trans-11-tetradecenal at the molecular ratio of approximately 1-cis-form to 9 trans-form, by reacting a Grignard reagent of 1,1-dialkoxy-9-halo-nonane with a mixture (approximately 60:40) of 1-chloro-2-pentene and 3-chloro-1-pentene and thereafter hydrolyzing thus formed 1,1-dialkoxy-11-tetradecene. 11-Tetradecenal is useful as a sex pheromone against the female eastern spruce budworm (*Choristoneura fumiferana*). The 9:1 ratio of trans/cis isomers is believed to be the most effective ratio to use against the budworms.

7 Claims, No Drawings

PROCESS FOR PREPARING INSECT PHEROMONES

This is a division of application Ser. No. 808,420, filed June 20, 1977.

This invention relates to the synthesis of the sex pheromone, 11-tetradecenal, of the female eastern spruce budworm (*Choristoneura fumiferana*) and intermediates therefor.

"Pheromone" is the name given to a wide variety of organic compounds which fulfill a quasi hormonal or more accurately communicational intra species role. The compounds in question, trans 11-tetradecenal and cis 11-tetradecenal as well as their respective reduction products, trans and cis 11-tetradecenol are the natural sex pheromones or sex attractants for a number of insect pests, among them the spruce budworm (*choristoneura fumiferana*). The female insect produces a minute amount of pheromone which is detected by the male of the species and aids him in finding and mating with the female. Sex pheromones have enormous potential in insect control as they appear to be harmless to other forms of life, and are relatively species specific. They may be used in a number of ways, eg., in trapping of male insects and in confusion of male insects so that they fail to find the female, thus preventing mating and reproduction.

The sex pheromone of the female eastern spruce budworm has been identified as a mixture of cis and trans 11-tetradecenal, J. Weatherston et al., Canadian Entomologist, Vol. 103, page 1741, 1971. The most effective ratio of cis and trans isomers is believed to be a mixture containing approximately 90% trans and approximately 10% cis isomers. The present invention provides means for the synthesis of 11-tetradecenal having directly the cis/trans isomer composition very close to that which is believed to be most effective for the trapping or disruption of the male budworm moth.

Almost all syntheses of long chain unsaturated compounds have in the past been based on joining, in the penultimate step, a straight chain difunctional alkane to an acetylenic hydrocarbon followed by partial reduction of the new acetylene to an olefin. 11-Tetradecenol has been prepared in this fashion [Roelofs, W. L., Arn, H. Nature 219, pg. 513 (1968) or J. Weatherstone et al., Canadian Entomologist, Vol. 103, pg. 1741 (1971)] in which the starting material is 10-bromo-1-decanol. This is a highly sophisticated organic intermediate and as such extremely expensive on a large scale. This material was blocked with dihydropyran (again a relatively sophisticated and expensive reagent) to gave the 10-bromo-1-tetrahydropyranyl decanane. This material was then reacted with the anion of 1-butyne in liquid ammonia to give 1-tetrahydropyranyl-11-tetradecyne. Such alkylations in liquid ammonia are expensive, difficult and often give poor yields. The material thus obtained was then either catalytically hydrogenated to give the cis olefin or reduced by dissolving metal in ammonia to give the trans olefin. The resulting cis or trans 1-tetrahydropyranyl-11-tetradecane was hydrolyzed to the cis or trans 11-tetradecenol.

The above synthesis is outlined in Table I below:

TABLE I

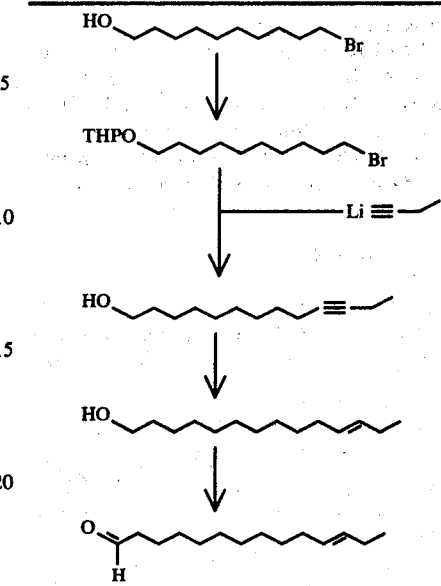

To convert this material to the aldehyde would require a painstaking selective oxidation. Such reactions give generally poor yields and are very expensive on a large scale.

An alternative synthesis appears to involve oxidation in the first step rather than the last, ie., 10-bromo-1-decanol oxidized to 10-bromo-1-decanal. This could then be blocked by alcohols to the 10-bromo-1,1-dialkoxy decane followed by steps similar to those outlined above.

All these and related syntheses suffer from the requirement of expensive starting materials and reagents and several inefficient steps.

An object of this invention is to provide a process for 11-tetradecenal which is simple and economical, and suitable for large scale production of the same.

Another object of this invention is to provide a process for 11-tetradecenal at the molecular ratio of about 9 trans-form to 1 cis-form.

A further object of this invention resides in the provision of a 1,1-dialkoxy-9-halo-nonane and a process therefor. The 1,1-dialkoxy-9-halo-nonane is useful as an intermediate for preparing 11-tetradecenal.

In one aspect of this invention, there is provided a compound having the formula:

(RO)$_2$CH(CH$_2$)$_7$CH$_2$X wherein each R separately denotes a (lower) alkyl and X is a halogen.

In another aspect of this invention, there is provided a process for preparing 11-tetradecenal comprising (1) treating a compound having the formula:

(RO)$_2$CH(CH$_2$)$_7$CH$_2$X wherein each R separately denotes a (lower) alkyl, and X is a halogen with at least an equimolecular amount of magnesium in an inert solvent selected from the group consisting of dialkyl ethers, cyclic ethers, and hydrocarbon solvents and the mixtures thereof to form a Grignard reagent having the formula:

(RO)₂CH(CH₂)₇CH₂MgX wherein R and X are defined above;

(2) reacting the Grignard reagent thus obtained with at least an equimolecular amount of 1-halo-2-pentene or 3-halo-1-pentene or a mixture thereof in an inert solvent selected from the group consisting of dialkyl ethers, cyclic ethers and hydrocarbon solvents and the mixtures thereof to form 1,1-dialkoxy-11-tetradecene of the formula:

(RO)₂CH(CH₂)₉(CH=CH)CH₂CH₃ wherein R is defined above; and (3) hydrolyzing the 1,1-dialkoxy-11-tetradecene with an aqueous acid to form 11-tetradecenal of the formula:

(OHC)(CH₂)₉(CH=CH)CH₂CH₃

In still another aspect of this invention, there is provided a process for preparing trans- and cis-11-tetradecenal at the molecular ratio of about 9 trans-form to 1 cis-form comprising:

(1) treating a compound having the formula:

(RO)₂CH(CH₂)₇CH₂X wherein each R separately denotes (lower) alkyl, and X is a halogen with at least an equimolecular amount of magnesium in an inert solvent selected from the group consisting of dialkyl ethers, cyclic ethers and hydrocarbon solvents and the mixtures thereof to form a Grignard reagent having the formula:

(RO)₂CH(CH₂)₇CH₂MgX wherein R and X are defined above;

(2) reacting the Grignard reagent thus obtained with at least an equimolecular amount of a mixture of approximately 40% by molecular ratio of 3-halo-1-pentene and approximately 60% by molecular ratio of 1-halo-2-pentene in an inert solvent selected from the group consisting of dialkyl ethers, cyclic ethers and hydrocarbon solvents and the mixtures thereof to form a mixture of trans- and cis-1,1-dialkoxy-11-tetradecene of the formula:

(RO)₂CH(CH₂)₉(CH=CH)CH₂CH₃ wherein R is defined above, at the molecular ratio of about 9 trans-form to 1 cis-form; and (3) hydrolyzing the mixture of trans- and cis-1,1-dialkoxy-11-tetradecene with an aqueous acid to form trans- and cis-11-tetradecenal at the molecular ratio of about 9 trans-form to 1 cis-form.

In a further aspect of this invention there is provided a process for preparing a compound having the formula:

(RO)₂CH(CH₂)₇CH₂X wherein each R separately denotes a (lower) alkyl, and X is a halogen, said process comprising reacting in a anhydrous alcohol having the formula ROH wherein R is a (lower) alkyl and in the presence of a strongly acidic catalyst a 9-halo-nonanal having the formula:

(OHC)(CH₂)₇CH₂X wherein X is defined above, in the presence of a dehydrating agent, such as, for example, excess alcohol, a trialkyl orthoformate having the formula HC(OR)₃ wherein R is defined above or anhydrous calcium sulfate, or a molecular sieve.

Further objects, advantages and aspects of this invention will become more apparent from the following detailed description of the present invention.

Table II is a schematic flow sheet showing the various reactions, not necessarily in their broadest aspects.

Table III shows certain of the reactions in somewhat more specific aspects.

A review of the coupling of Grignard reagents with alkyl and alkenyl halides can be found in "*Grignard Reactions of Non-Metallic Substances,*" M. S. Kharasch, page 1046–1086, (New York, Prentice-Hall, Inc., 1954). There is disclosed at Page 1086 thereof reactions similar to the coupling of pentenyl chloride with the Grignard reagent from 1,1-dialkoxy-9-halo nonane.

The ozonolysis can be conducted so as to give either 9-halo-nonaldehyde or directly 1,1-dialkoxy-9-halo nonane. The former procedure has been described by C. R. Noller and R. A. Bannerot, *J.A.C.S.*, 56, 1963 (1934). The latter procedure has not, to our knowledge, been previously described. However, the dialkyl sulphide method of ozonide reduction is disclosed in British Pat. No. 1,092,615 published Nov. 29, 1967.

GENERAL PREPARATION

Oleyl alcohol is converted to oleyl chloride by the action of either phosphorous pentachloride or thionyl chloride in hydrocarbon solvent at a temperature from 0° C. to 150° C. The chloride is isolated and distilled. The boiling point at 3 torr is about 165° C.

The oleyl halide may be ozonized in either acidic, hydrocarbon, chlorinated or hydroxylic solvent, and the resulting ozonide may be reduced either catalytically or by dissolving metal (or related reaction) or by iodide salts or by addition of alkyl sulfides to either 9-halo-nonanal or 1,1-dialkoxy-9-halo nonane.

TABLE II

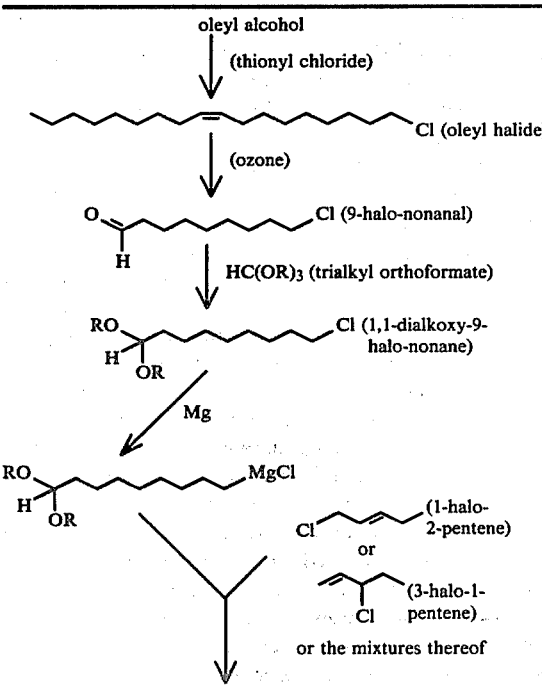

TABLE II-continued

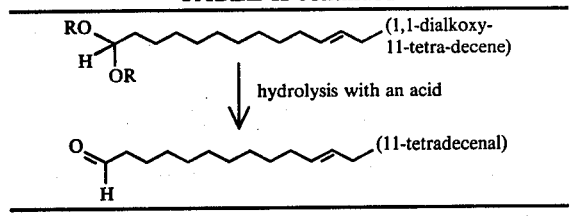

TABLE III cis and trans 11-TETRADECENAL

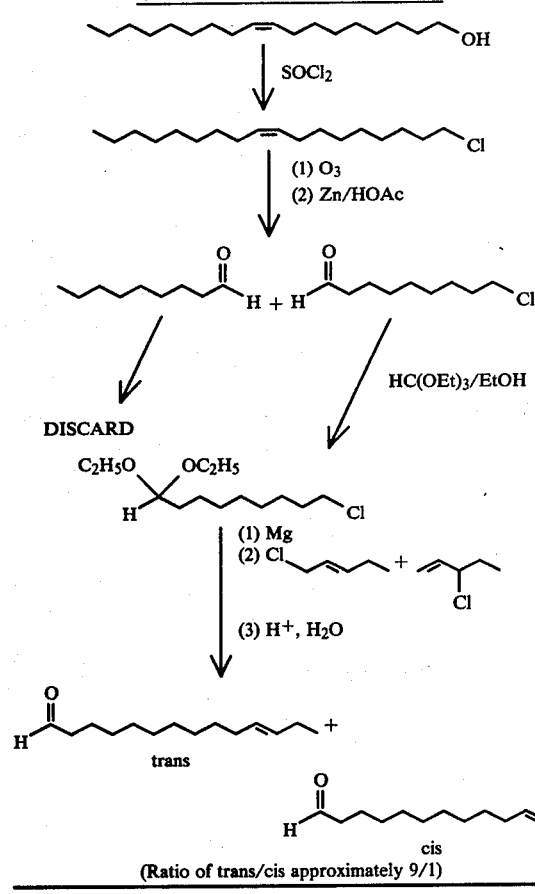

(Ratio of trans/cis approximately 9/1)

In the former case, the 9-halo-nonanal is then converted by acetalization to 1,1-dialkoxy-9-halo nonane. The latter procedure is accomplished by ozonolysis of oleyl halide in an anhydrous alcoholic solvent such as methanol followed by reduction of the ozonide by either catalytic hydrogenation or by addition of dialkyl sulfides. The resulting alcoholic solution is directly treated with catalytic amounts of acid in the presence of inorganic water-insoluble dehydrating agents, such as calcium sulphate. Other types of dehydrating agents may be used, such as a molecular sieve.

It may not be necessary to treat the resulting alcoholic solution with such a dehydrating agent provided that the reaction is carried out in the presence of excess anhydrous alcohol generally at least 3 to 10, or especially 5 to 10 times the stoichiometric amount of 9-halo-nonanal in molecular ratio.

The resulting 1,1-dialkoxy-9-halo nonane is then isolated by evaporation of the alcoholic solvent followed by fractional distillation. The 1,1-dialkoxy-9-halo nonane is then converted to 11-tetradecenal by a Grignard coupling reaction with either 1-halo-2-pentene or 3-halo-1-pentene or a mixture of the two. The coupling is accomplished by conversion of the 1,1-dialkoxy-9-halo nonane to the Grignard derivative by treatment with magnesium in either dialkyl or cyclic ether or hydrocarbon solvents or a mixture of the above at a temperature suitable to the particular solvent used, usually between 70° and 80° C. The solution of Grignard derivative is then treated with the halo pentene solution in the same or in different solvent.

The reaction will behave differently depending on the particular magnesium compound formed in the Grignard reaction. Magnesium chloride and bromide are examples.

The product of this reaction is actually 1,1-dialkoxy-11-tetradecene. However, this compound is directly hydrolysed to 11-tetradecenal by agitation and heating of the above reaction mixture with aqueous acid. The resulting 11-tetradecenal is then isolated in the usual fashion by extraction and distillation. The product thus obtained is a mixture of trans and cis 11-tetradecenal and 10-ethyl-11-dodecenal.

The preferred proportions of trans compound to cis appears to be in the area of 85–95% trans to 5–15% cis. The most preferred ratios seem to be in the area of 90 or 93 trans to 10 or 7 cis.

The composition produced by the present process depends somewhat upon reaction conditions but is generally found to be close to the following ratio, 8% cis 11-tetradecenal, 72% trans 11-tetradecenal and 20% 10-ethyl-11-dodecenal. The contaminating 10-ethyl-11-dodecenal is easily separated from the cis and trans 11-tetradecenal by fractional distillation. During this fractional distillation, the ratio of trans to cis 11-tetradecenal is unaltered. Catalysis of the coupling reaction by transition metal salts results in variation in the product composition thus providing some control of the isomer ratios. Reduction of the cis/trans isomer mixture of 11-tetradecenal by a variety of common means, such as sodium borohydride, results in the same cis/trans isomer composition of 11-tetradecenol. These latter compounds or their acetates are natural sex attractants in a variety of other insect species.

Following the examples hereinafter, it is possible to prepare an essentially 1 to 9 mixture of 11-cis to 11-trans isomers directly through synthesis.

The following examples are provided to illustrate the practise of the invention. Temperature is given in degrees centrigrade.

EXAMPLE 1

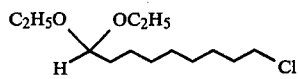

67 gms of oleyl alcohol was dissolved in 75 mls of benzene, 0.15 ml of pyridine were added. The solution was cooled to 0° C. and 46 gms of thionyl chloride was added over 5 minutes with stirring. The solution was heated to reflux temperature for 10 minutes until all sulphur dioxide evolution ceased. It was cooled and extracted with 150 ml of 10% saline solution then with 50 ml of 10% sodium carbonate solution and finally with 100 ml of 10% saline solution. The organic layer was dried over sodium sulphate, evaporated and distilled. The product distilled at 166°–169° C., at 3 torr and yielded 58 gms of oleyl chloride.

28.6 gms of oleyl chloride is dissolved in 60 mls of glacial acetic acid. Ozone (approximately 5%) is bubbled through the solution at room temperature for two hours. At the end of this time, a test with bromine in acetic acid showed that no olefin remained in the reaction. The reaction mixture was then diluted with 100 mls of diethyl ether in a 500 ml flask with condenser and magnetic stirrer. To this solution was added 2 gms of powdered zinc and 0.2 ml of water. Then over a period of ten minutes, 18 gms of zinc were added in small portions. Then 4 mls of water were added slowly. The mixture was heated at reflux temperature for 20 minutes until no reaction was observed with starch/iodide solution. The reaction was cooled, filtered and extracted twice with 50 mls of water, once with 50 ml of 10% sodium carbonate and finally with 50 ml of saline solution. The solution was dried over calcium chloride, concentrated on rotary evaporator and distilled. The fraction collected at 95° to 105° at 0.3 torr weighed 12.0 gms and consisted of essentially pure 9-chloro-nonaldehyde.

12.0 gms of 9-chloro-nonaldehyde was heated at reflux with 20 gms of triethyl orthoformate, 9 gms anhydrous ethanol and one drop of concentrated sulphuric acid for one hour. The reaction was cooled, 10 gms of sodium carbonate was added and the mixture stirred 10 minutes. The mixture was diluted with 100 mls of diethyl ether and extracted twice with 50 mls of saline solution. The organic layer was dried over sodium sulphate, concentrated on rotary evaporator and distilled. The major fraction distilled at 84° at 0.1 torr yielding 13.3 gms of 1,1-diethoxy-9-chloro nonane. N.M.R. (CdCl$_3$): triplet 4.47 ppm (1H), multiplet 3.58 ppm (6H), triplet 1.21 ppm.

EXAMPLE 2

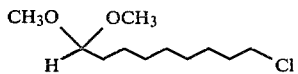

57.2 gms of oleyl chloride is dissolved in 200 mls of anhydrous methanol. Ozone (approximately 5%) is bubbled through the solution (cooled in an ice bath) for approximately four hours. At the end of this time, a test with bromine and acetic acid showed that no olefin remained in the reaction. 20 mls of dimethyl sulphide were then added to the reaction flask which was then allowed to stand at ice temperature for one hour. The flask was removed from the ice bath and stood for a further one half hour. To the reaction flask was now added 0.25 mls of concentrated sulphuric acid. The solution was refluxed over 150 gms of anhydrous calcium sulphate in a soxhlet extractor overnight. The reaction was cooled, 1 gm of anhydrous calcium carbonate was added and allowed to stir for approximately 15 minutes. The reaction was filtered, the solvent removed on rotary evaporator, and the residue fractionally distilled. Material distilling between 74° and 88° at 0.1 torr was collected. The yield of 1,1-dimethoxy-9-chloro nonane was 34 gms. Redistillation yielded material boiling at 70° C. at 0.08 torr. N.M.R. (CdCl$_3$): triplet 4.34 ppm (1H), triplet 3.53 ppm (2H), singlet 2.32 ppm (6H) M.S. (m/e: 191, 193; 190, 192; 71).

EXAMPLE 3

To 0.85 gm of magnesium in a thoroughly dried flask equipped with condensor and magnetic stirrer was added 5 mls of anhydrous tetrahydrofuran and 1.06 mls of butyl chloride and 5 mls of dry toluene. This mixture was heated with stirring at 70° C. for about two hours. A solution of 4.44 gms of 1,1-dimethoxy-9-chloro nonane in 50 mls of toluene was added all at once. The temperature was maintained at 75°±5° for one and one quarter hours. The Grignard reagent was decanted into another flask and 3.12 gms of a mixture (approximately 60:40) of 1-chloro-2-pentene and 3-chloro-1-pentene was added. The reaction was maintained at 75°±5° with stirring. The reaction mixture became cloudy within one-half to three-quarters of an hour indicating the initiation of the coupling reaction. This was confirmed by GLC of a hydrolysed aliquot of reaction mixture. The reaction was allowed to continue until a test for Grignard reagent was negative (approximately 2 hours). 50 mls of 3 N hydrochloric acid was then added, the reaction mixture was then stirred and heated at reflux for 1 hour. The aqueous layer was separated, washed two times with toluene. The organic layer and the toluene washes were combined and dried over sodium sulphate. The solvents were removed on the rotary evaporator and the residue was distilled. The majority of the material distilled at 95° at 0.35 torr yielding 2.48 gms of crude 11-tetradecenal. For physical constants see Example 5.

Gas Liquid Chromatographic (GLC) analysis of this material shows it to contain approximately 20% 10-ethyl-11-dodecenal, approximately 8% cis 11-tetradecenal and approximately 72% trans 11-tetradecenal. The branch chain isomer 10-ethyl-11-dodecenal can be readily removed by fractional distillation of this material.

EXAMPLE 4

To 0.85 gm of magnesium in a thoroughly dried flask equipped with condensor and magnetic stirrer was added 5 mls of anhydrous tetrahydrofuran and 0.5 ml of dibromo ethane. A solution of 4.5 gms of 1,1-dimethoxy-9-chlorononane in 40 mls of toluene was added dropwise. When addition was half complete, a few drops of bromoethane were added and the addition was continued. The temperature was maintained at 75°±5° for two hours. The Grignard reagent was decanted into another flask and 100 mgs of cuprous chloride (CuCl) catalyst was added, followed by dropwise addition of 3.0 gms of a mixture (approximately 60:40) of 1-chloro-2-pentene and 3-chloro-1-pentene dissolved in 15 mls of toluene. The reaction flask was cooled in a water bath at 20°±5°. Magnesium chloride began to precipitate after ten minutes. The reaction stood overnight at room temperature. 50 mls of 3 N hydrochloric acid was added and the reaction mixture was stirred and heated at reflux for 1 hour. The aqueous layer was separated and washed two times with toluene. The organic layer and the toluene washes were combined and dried over sodium sulphate. The solvents were removed on the rotary evaporator and the residue was distilled at 83° at 0.10 torr yielding 2.3 gms of crude 11-tetradecenal. GLC analysis showed that the contaminating 10-ethyl-11-dodecenal was present in only 11.5%. For physical constants see Example 5.

EXAMPLE 5

To 0.48 gm of magnesium in a thoroughly dried flask equipped with condenser and magnetic stirrer was added 2 mls of anhydrous tetrahydrofuran and 0.3 ml of butyl chloride. The mixture was stirred and heated at reflux until reaction initiated (approximately 10 minutes). After 5 minutes, portionwise addition of 3.5 gms of 1,1-diethoxy-9-chloro nonane in 10 ml of tetrahydrofuran was begun. When the addition was complete (15 minutes) the mixture was stirred and heated for 2 hours. It was then cooled to 5° C. in an ice bath and 30 gms of a mixture of 3-chloro-1-pentene (approximately 40%) and 1-chloro-2-pentene (approximately 60%) was added all at once. The mixture was heated slowly and stirred, whereupon it became cloudy. Heating was continued at reflux temperature for 2 hours. The mixture was then cooled, poured into 100 ml of 3 N-hydrochloric acid and diluted with 100 ml of tetrahydrofuran and 150 ml of acetone. The resulting solution was stirred and heated for 30 minutes. It was then concentrated on rotary evaporator and extracted twice with 100 mls of hexane. The organic layer was dried over sodium sulphate, evaporated and distilled. The majority distilled at 110° C. at 0.35 torr and yielded 2.11 gms of 11-tetradecenal.

Identity of 11-tetradecenal has been established as follows: retention time (7.8 minutes) on gas chromatography (6 foot×¼ inch column OV-1, 145° C., flow rate 20 mls per minute), by mass spectroscopy (m/e: 210(M+), 192, 163, 149), by proton magnetic resonance [9.74 ppm multiplet (1H), 5.40 ppm multiplet (2H)], and infrared spectroscopy (peaks at: 1730 cm$^{-1}$, 2725 cm$^{-1}$, 2860 cm$^{-1}$ and 970 cm$^{-1}$. The isomeric 10-ethyl-11-dodecenal was identified by its mass spectrum: (m/e: 210(M+), 192, 163).

The embodiments of the invention in which an exclusive property or privilege is claimed are defined as follows:

1. A process for preparing trans- and cis-11-tetradecenal at the molecular ratio of about 9 trans- form to 1 cis- form which comprises:
   (1) treating a compound of the formula:

$(RO)_2CH(CH_2)_7CH_2X$ wherein each R separately denotes (lower) alkyl, and X is a halogen with at least an equimolecular amount of magnesium in an inert solvent selected from the group consisting of dialkyl ethers, cyclic ethers and hydrocarbon solvents and the mixtures thereof to form a Grignard reagent having the formula:

$(RO_2)CH(CH_2)_7CH_2MgX$ wherein R and X are defined above;
   (2) reacting the Grignard reagent thus obtained with at least an equimolecular amount of a mixture of approximately 40% by molecular ratio of 3-halo-1-pentene and approximately 60% by molecular ratio of 1-halo-2-pentene in an inert solvent selected from the group consisting of dialkyl ethers, cyclic ethers and hydrocarbon solvents and the mixtures thereof to form a mixture of trans- and cis-1,1-dialkoxy-11-tetradecene of the formula:

$(RO)_2CH(CH_2)_9CH=CH)CH_2CH_3$ wherein R is as defined above, at the molecular ratio of about 9 transform to 1 cis- form; and
   (3) hydrolyzing the mixture of trans- and cis-1,1-dialkoxy-11-tetradecene with an aqueous acid to form trans- and cis-11-tetradecenal at the molecular ratio of about 9 trans- form to 1 cis- form.

2. The process as in claim 1 wherein in the first and second steps each corresponding R separately denotes methyl or ethyl.

3. The process as in claim 1 wherein in the second step the reaction is carried out in the presence of a catalyst.

4. The process as in claim 3 wherein in the second step the catalyst is cuprous chloride.

5. The process as in claim 1 wherein in the first and second steps the reaction is carried out at a temperature of between 70° and 80° C.

6. The process as in claim 1 wherein in each of the first and second steps the inert solvent is a mixture of tetrahydrofuran and toluene.

7. The process as in claim 1 wherein the aqueous acid is aqueous hydrochloric or sulphuric acid.

* * * * *